United States Patent [19]
Behnke et al.

[11] Patent Number: 5,520,641
[45] Date of Patent: May 28, 1996

[54] IV INJECTION AND SAMPLING SITE HAVING SEPTUM WITH MULTIPLE OPENINGS

[75] Inventors: Brett A. Behnke, Hastings; Gary A. Thill, Vadnais Heights, both of Minn.

[73] Assignee: Minnesota Mining and Manufacturing Company, St. Paul, Minn.

[21] Appl. No.: 384,403

[22] Filed: Feb. 6, 1995

[51] Int. Cl.⁶ .................................................. A61M 37/00
[52] U.S. Cl. ........................... 604/86; 604/256; 604/283; 604/905; 604/28
[58] Field of Search .................................. 604/86, 88, 30, 604/167, 244, 256, 411, 415, 905, 83, 91, 246–247, 283–284; 128/764, 766; 251/149.1; 215/247

[56] References Cited

U.S. PATENT DOCUMENTS

| | | |
|---|---|---|
| 3,977,400 | 8/1976 | Moorehead . |
| 5,100,394 | 3/1992 | Dudar et al. . |
| 5,167,648 | 12/1992 | Jepson et al. . |
| 5,171,234 | 12/1992 | Jepson et al. . |
| 5,188,620 | 2/1993 | Jepson et al. . |
| 5,211,634 | 5/1993 | Vaillancourt . |
| 5,211,638 | 5/1993 | Dudar et al. . |
| 5,300,034 | 4/1994 | Behnke et al. . |
| 5,351,383 | 10/1994 | Behnke et al. . |
| 5,354,275 | 10/1994 | Behnke et al. . |
| 5,400,500 | 3/1995 | Behnke et al. . |
| 5,405,331 | 4/1995 | Behnke et al. . |

FOREIGN PATENT DOCUMENTS

| | | |
|---|---|---|
| 8124084 U | 8/1981 | Germany . |
| 3303718 | 10/1984 | Germany . |
| WO94/03373 | 2/1994 | WIPO . |

OTHER PUBLICATIONS

Special Report and Product Review, "Needlestick–Prevention Devices"; Health Devices, vol. 20, No. 5, May 1991, pp. 154–180.

Primary Examiner—Randall L. Green
Assistant Examiner—Perry E. Van Over
Attorney, Agent, or Firm—Gary L. Griswold; Walter N. Kirn; Stephen W. Bauer

[57] ABSTRACT

The present invention provides a reliable, leak-resistant site for the introduction of blunt or sharp penetrators and includes an elastomeric septum through which multiple openings are formed in the axial direction. The septum is inserted within a housing having a passageway defining an axial direction. The present invention also includes a method of using the injection or sampling site along with a method of assembling the same.

25 Claims, 4 Drawing Sheets

5,520,641

IV INJECTION AND SAMPLING SITE HAVING SEPTUM WITH MULTIPLE OPENINGS

FIELD OF THE INVENTION

The present invention relates to infusion therapy and IV injection or sampling sites, and more particularly to an IV injection or sampling site adapted to receive a blunt cannula.

BACKGROUND OF THE INVENTION

In an effort to reduce the risk of transmitting infectious diseases, such as hepatitis and AIDS, via accidental needle sticks, various designs of IV injection sites have been developed that are adapted to receive a blunt cannula and/or shielded cannula. See, e.g., Special Report and Product Review, Needlestick-Prevention Devices, Health Devices, pages 154–180 (ECRI, Plymouth Meeting, Pa. 1991). One approach has been to employ a slit septum Y-site in which a slit elastomeric septum is compressed in the Y-site housing. A blunt cannula can be introduced through the slit of the septum, and assuming the design works as intended, the septum will seal against the cannula shaft. When the cannula is removed, the septum seals itself.

Injection sites of this type are either available from or publicized by Baxter International, Inc., Deerfield, Ill., under the trade designation "Baxter's Needle-Less Injection Sites"; Abbott Laboratories, Inc., Abbott Park, Ill., under the trade designation "Safe-Line No-Needle I.V. System". A blunt cannula has been available from Becton, Dickinson and Company, Paramus, N.J., under the trade designation "Interlink System".

In many of these systems the slitting of the septum is critical to their proper functioning. The slitting of the septum often requires precise accuracy in the location and dimensions of the slit. Moreover, custom-made tools, secondary operations and subsequent testing are often required to form acceptable leak-resistant slits.

In at least some of these injection sites having slit septums, the manufacturer instructs the user that sharp needles, if used, should be inserted through the septum near its perimeter to avoid creating a leak through the slitted portion of the septum. This practice contradicts the training of health care personnel who are taught to insert needles through the centers of septums to help prevent inadvertent needlestick injuries with their attendant complications.

SUMMARY OF THE INVENTION

The housing and septum of the present invention provides an injection or sampling site which is reliable and leak-resistant and can be used with blunt or sharp penetrators.

In one preferred embodiment, the site comprises an elastomeric septum through which multiple openings are formed in the axial direction. The openings are located generally about the center of the septum. The septum is inserted within a housing having a passageway defining an axial direction. The relationship between the outside diameter of the septum and the inside diameter of the passageway are such that the septum is compressed in the radial direction to seal the openings formed therethrough.

The present invention further includes a method of using the housing and septum according to the present invention and a method of assembling the same.

Advantages of the invention include the ability to insert both blunt and sharp penetrators through the center area of the septum. As such, the sites manufactured according to the present invention allow health care practitioners to use the safest procedures for injection or sampling to reduce the chances of needlestick injuries and their attendant complications.

Each of the openings is preferably sized to receive a cannula without tearing due to the elastic nature of the septum. As a result, multiple entry points for blunt cannulas are provided, thereby eliminating the need to accurately center the cannula before inserting it through single slit.

Another advantage of the present invention is that it eliminates the difficulties in accurately cutting a slit in the center septum.

These and other features and advantages of the invention will be in part apparent upon a reading of the detailed description below and with reference to the drawings and claims.

BRIEF DESCRIPTION OF THE DRAWINGS

Corresponding reference numerals indicate corresponding parts throughout several views of the drawings.

DETAILED DESCRIPTION OF PREFERRED EMBODIMENTS

Figure 1:
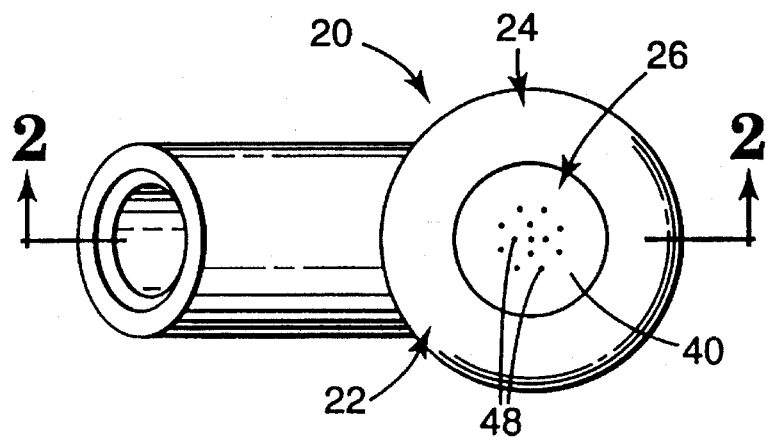
FIG. 1 is a top plan view of the Y-site IV injection site incorporating a first embodiment of an injection site constructed according to the principles of this invention.
Figure 2:
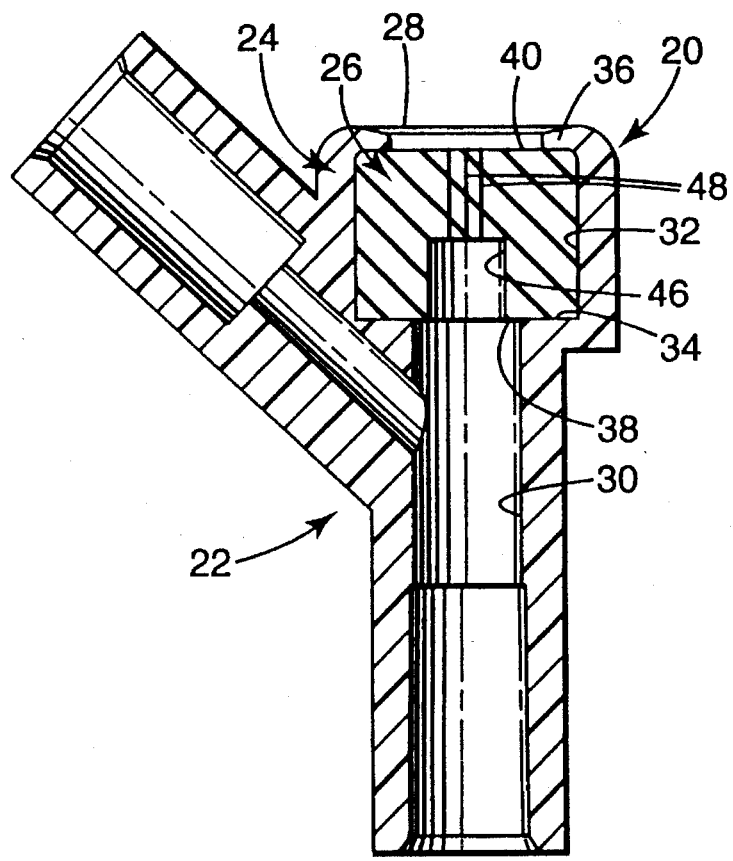
FIG. 2 is a longitudinal cross-sectional view of the Y-site IV injection site, taken along the plane of line 2—2 in FIG. 1.

One preferred embodiment of an injection or sampling site constructed according to the principles of this invention, indicated generally as 20, is shown in FIGS. 1 and 2 as it would be incorporated into a Y-site IV injection site. It will be understood that the invention is not so limited and can be applied to any type of medical injection or sampling sites, for example IV administration tubing sets, or drug vials, etc.

As shown in FIGS. 1 and 2, the injection site 20 comprises a housings 24 and a septum 26. The housing 24 has an outside end 28 and a passageway 30 extending inwardly from the outside end. The passageway 30 defines an axial direction.

The passageway 30 includes a septum-receiving portion 32, which in this preferred embodiment is generally cylindrical, with a generally circular cross section. The inner end of the septum-receiving portion 32 is defined by a ledge or shoulder 34 in the passageway 30, and the outer end of the septum-receiving portion is defined by a ledge or flange 36 for retaining the septum 26 in the housing 24.

The septum 26 is preferably made from any suitable elastomeric material, such as, for example, the natural rubber available under the trade designation "5135 Rubber" from the West Co., Lionville, Pa. Other suitable elastomeric materials include natural or synthetic polyisoprene. The most preferred polyisoprene materials are synthetic and have a durometer of approximately 35 on the Shore A scale and a compression set of approximately 16.4%. Suitable polyisoprene materials include "5218 or 5251 Gum Rubber" available from Abbott Laboratories, Inc., Abbott Park, Ill.; "1028 GUM Rubber" and Catalog Nos. "2-2-3 7389-35" and "2-6-2X 7389-35" available from The West Company, Phoenixville, Pa.; and Catalog No. "L 3819" available from Neff Perkins Co., Painesville, Ohio. A silicone formulation available under Catalog No. "L 4795" from Neff Perkins Co. may also be suitable.

The housing 24 is preferably formed of relatively rigid synthetic resin material, such as copolyester material available under the trade designation "DN003" from Eastman Chemical Co., Kingsport, Tenn. Any material would, however, be suitable for the housing provided it has sufficient rigidity to compress the septum 26.

Figure 3:
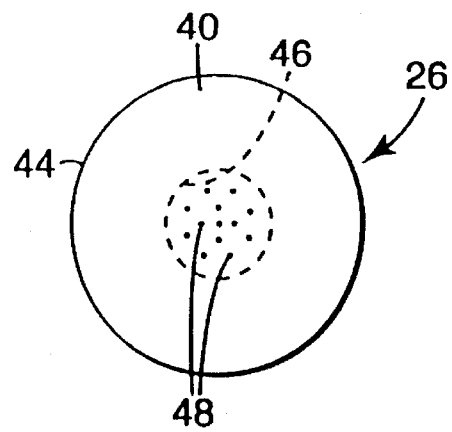
FIG. 3 is a top plan view of the septum before assembly into the injection site of FIGS. 1 and 2.
Figure 4:
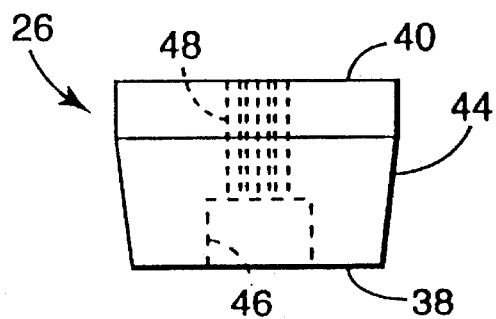
FIG. 4 is side elevation view of a septum before assembly into the injection site of the first embodiment, with the openings 48 and-bore 46 depicted as hidden lines.
Figure 5:
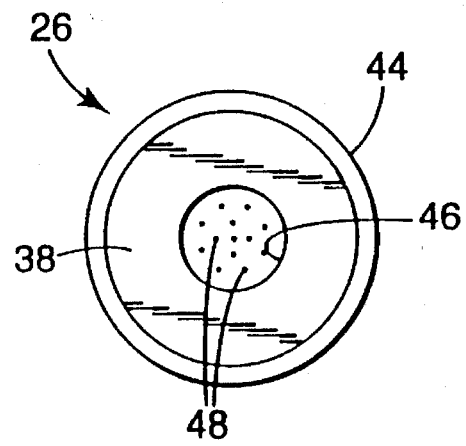
FIG. 5 is a bottom plan view of the septum before assembly into the injection site of FIGS. 1 and 2.

The septum 26 is closely received in the septum-receiving portion 32 of the passageway 30 of the housing 24. The septum 26 has inside and outside ends 38 and 40, respectively. The ends of the septum are generally circular, as shown in FIGS. 3 and 5. The outside end 40 of the septum 26 is generally larger in diameter than the inside end of the septum 26, as shown in FIG. 4. The inside end 38 of the septum 26 abuts the shoulders 34 in the passageway 30. The flange 36 retains the outside end 40 of the septum in the housing 24. The septum 26 is held captive between the shoulder 34 and flange 36 such that when a blunt cannula C is pressed against the outside end 40 of the septum 26 the cannula C tends to pass through any one of openings 48, as opposed to substantially displacing the septum 26.

One preferred method and apparatus for swaging the housing to form the flange 36 is described in coassigned U.S. Pat. No. 5,351,383, which is hereby incorporated herein by reference.

The septum 26 could also be secured in the housing with an adhesive. That construction may allow the flange 36 to be eliminated. Suitable adhesives may include (a) cyclohexanone available from EM Industries, Inc., Gibbstown, N.J.; (b) cyanoacrylate instant adhesive under the trade designation "CA-40" from Minnesota Mining and Manufacturing Company, St. Paul, Minn.; or (c) an Ultraviolet curable adhesive such as available under the trade designation "LOCTITE 3301 medical grade UV curable adhesive" from Loctite Corp., Newington, Conn.

The septum 26 could also be provided with a tubular extension (not shown) on the outside end, that could be folded over the exterior of the housing to secure the septum in the housing, as is known in the art.

Referring to FIGS. 3–5, a preferred septum 26 comprises a generally frustoconical inner portion 42, adjacent the inside end 38, and a generally cylindrical outer portion 44. The outer portion 44 has a generally constant diameter throughout its length, and the inner portion 42 has a generally frustoconical configuration tapering downwardly from the generally larger circular cross section of the outer portion 44 to the generally smaller circular cross-section of the inside end 38, as disclosed in co-assigned U.S. Pat. No. 5,300,034 and allowed U.S. patent application Ser. No. 08/072,512, filed Jun. 4, 1993, by Brett A. Behnke and Gary A. Thill, both of which are incorporated herein by reference. This taper facilitates the insertion of the septum 26 into the passageway 30 of the housing 24. The taper of the frustoconical inner portion 42 also insures that radial compression of the septum 26 in the housing 24 will be greater generally adjacent the outside end 40 of the septum 26 than adjacent the inside end 38 of the septum 26. This is believed to improve performance of the septum 26. It will, however, be understood that the septum 26 could be provided with a constant diameter along its axial length.

Preferably, a bore 46 extends generally axially into the septum 26 from the inside end 38. The bore 46 preferably extends about 25% to about 50% of the way through the septum 26. As explained below, the bore 46 preferably has a generally circular cross-section, although other shapes may be substituted. Co-assigned U.S. Pat. Nos. 5,300,034; 5,351,383 and 5,354,275, and allowed U.S. patent application Ser. Nos. 08/072,512, filed Jun. 4, 1993, and 08/269,849, filed Jul. 1, 1994, which are hereby incorporated herein by reference, disclose septums having a bore extending into the septum from the inside end of the septum.

Figure 6:
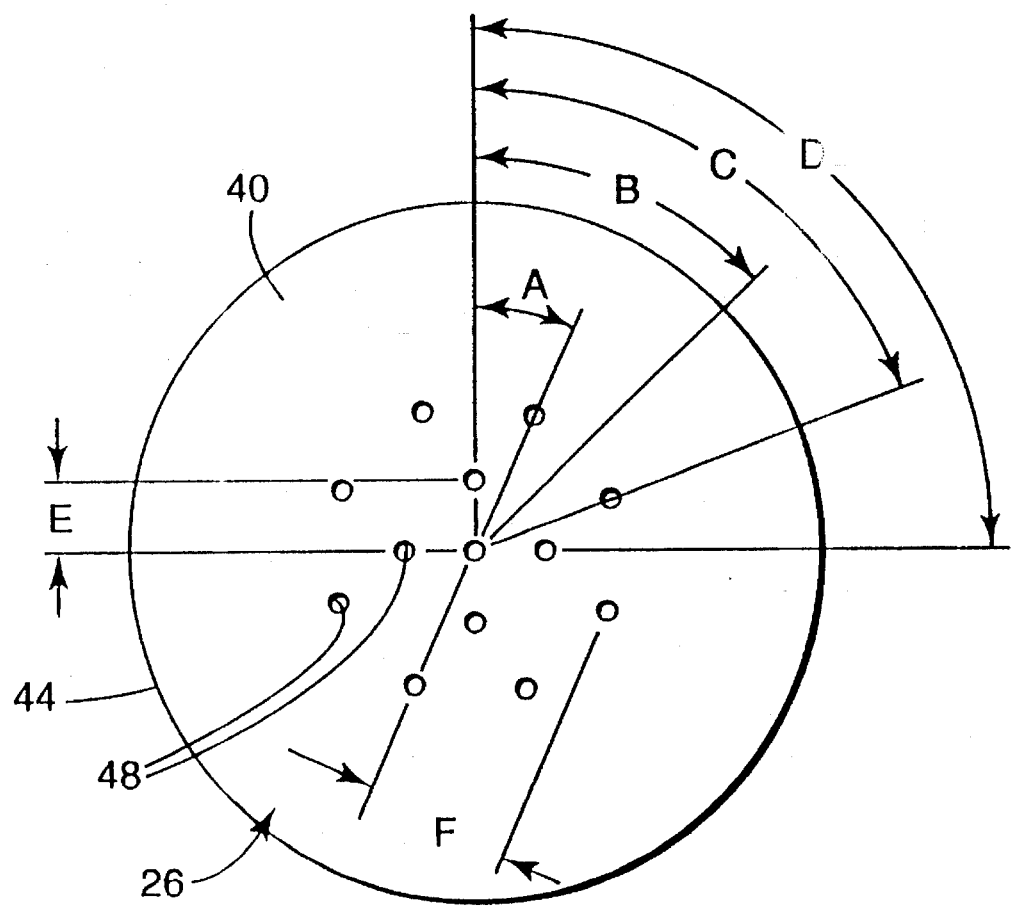
FIG. 6 is a schematic diagram indicating one pattern for openings in a septum according to the present invention.

A plurality of openings 48 extend generally axially through the septum 26 from the outside end 40 to the bore 46. It is preferred that about 5–30 openings be provided and that they be arranged in a generally circular pattern about the center of the septum 26 as depicted in FIGS. 4 and 6. Most preferably, at least ten openings 48 (e.g., fifteen openings 48) are provided. It is preferred that the area containing the openings 48 occupy an area having a diameter of about 25–50% of the diameter of the septum 26 at its outer end 40. For example, in a septum 26 having an outer diameter of approximately 0.25 inches (6.4 mm), the openings 48 are distributed about an area having a diameter of approximately 0.125 inches (3.2 mm).

FIG. 6 depicts one pattern of openings 48 used in a septum 26 according to the present invention. The pattern includes twelve openings spaced about a central opening in two generally circular patterns. The inner circle includes four openings 48 spaced equidistant from the center of the septum 26 and offset about 90° from its neighbors, as illustrated by the angle D in FIG. 6. The outer circle includes eight openings 48 also located equidistant from the central opening 48, with each opening 48 offset from its neighbors by about 45°, as illustrated by the angle C in FIG. 6.

Most preferably, the openings 48 of the outer circle may be spaced approximately twice as far from the central opening 48 as the openings of the inner circle. For example, the four openings 48 of the inner circle may be spaced from the Central opening 48 by a distance E of approximately 0.031 inches (0.29 mm), and the eight openings 48 of the outer circle may be spaced from the central opening 48 by a distance F of approximately 0.062 inches (1.57 mm).

As shown at angle A in FIG. 6, it is preferred that the openings 48 in the outer circle do not lie along the same radial line from the center of the septum 26 as do the openings 48 in the inner circle. For example, angle A illustrates an opening 48 of the outer circle being offset radially by an angle of approximately 22.5° from its closest opening 48 of the inner circle. Angle B is approximately 45°, and represents an example of the angle between an opening 48 of the inner circle and a point defined by the midpoint between the closest two openings 48 of the outer circle along one side of the aforesaid opening 48.

It will be understood that the pattern and spacing of the openings 48 depicted in FIG. 6 is only one example and that many variations could be substituted within the scope of the present invention.

In those embodiments which include a bore 46 formed in the inner end of the septum, it is further preferred that the openings 48 be located directly above the bore 46 and open into the same to facilitate insertion of the penetrators through the bore 46.

The arrangement is such that when a blunt cannula C is introduced through any one of the openings 48 in the septum 26, the elastomeric material of the septum 26 expands into the bore 46 of the septum to facilitate insertion of the cannula C through the opening 48 in the septum 26. See FIGS. 7 and 8. The arrangement of the bore 46 in the septum 26 is preferably such that when a cannula C is introduced through any of a plurality of openings 48 in the septum 26, the cannula C displaces elastomeric material of the septum 26 such that the elastomeric material of the septum 26 is diverted or expanded into the bore 46 of the septum 26 to sealingly engage the cannula C along the bore 46 of the septum 26. For example, the septum 26 is constrained within the septum-receiving portion 32 of the passageway 30 of the housing 24 between two ledges. When the elastomeric material of the septum 26 is displaced by a cannula C it will be diverted toward the bore 46 to reduce the diameter of the bore 46 of the septum.

Figure 9:
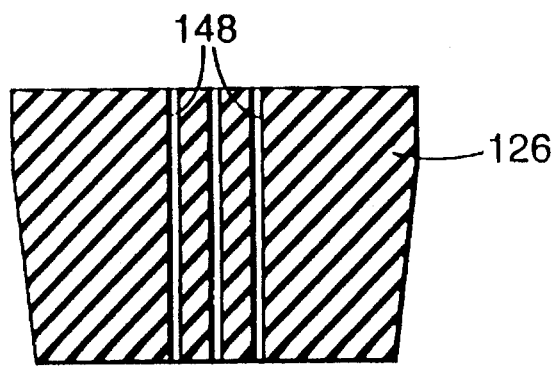
FIG. 9 is a cross-sectional side view of an alternate preferred septum according to the present invention.

While it is preferred that the septum 26 include a bore 46 to allow for displacement of the septum material and to provide additional sealing between the cannula and the bore 46, it will be understood that the septum 26 could be provided with the openings 48 but not the bore 46, as illustrated in FIG. 9.

The openings 48 can be formed in the septum 26 by piercing with small pins, trocars or blades. Suitable instruments used for piercing could include 0.095" (2.4 mm) three-sided veterinary needle, 0.050" (1.3 mm) chisel-tipped blade or a 0.035–0.050" (0.9–1.3 mm) deflected point or standard needle. Most preferably, a standard point needle having a diameter of approximately 0.035 inches (0.9 mm) is used, with the point of the needle cutting the hole and the shaft merely elastically stretching the hole. The resulting hole is substantially smaller than the diameter of the needle. Alternatively, if a chisel-tipped blade having a 0.05 inches (1.3 mm) long cutting edge is employed, which is not the most preferred method, the septum and blade should be aligned such that the resulting elongate slit-shaped holes are aligned with one another, without intersecting slits.

The plurality of openings 48 can be pierced by an array of such instruments or they can be formed sequentially by a single instrument. In one embodiment, openings 48 were pierced while the septum 26 was under compression in a housing 24 although it will be understood that the openings 48 could be formed while the septum 26 was not compressed. Alternatively, preferably the openings can be formed while the septum 26 is held in a septum-receiving bore as disclosed in U.S. Pat. No. 5,351,383, which is incorporated herein by reference.

Alternately, the septum 26 can be molded, for example by injection molding, with the openings 48 formed therein. That molding process can be an integral molding process in which the septum is molded in one continuous piece, as opposed to a number of pieces mechanically positioned together.

The septum 26 is then installed in the housing 24. The smaller diameter of the inner end 38 and the tapering configuration of the inner portion 42 facilitate the insertion of the preferred septum 26 into the housing 24.

The outside diameter of the outer end 40 of the septum 26 is preferably larger than the inner diameter of the corresponding portion of the housing 24. As a result, the septum 26 is compressed radially towards the axial center of the septum 26 and passageway 32. This compression assists in the sealing of openings 48 to prevent leakage as well as sealing between the septum 26 and the housing 24.

Figures 7, 8:
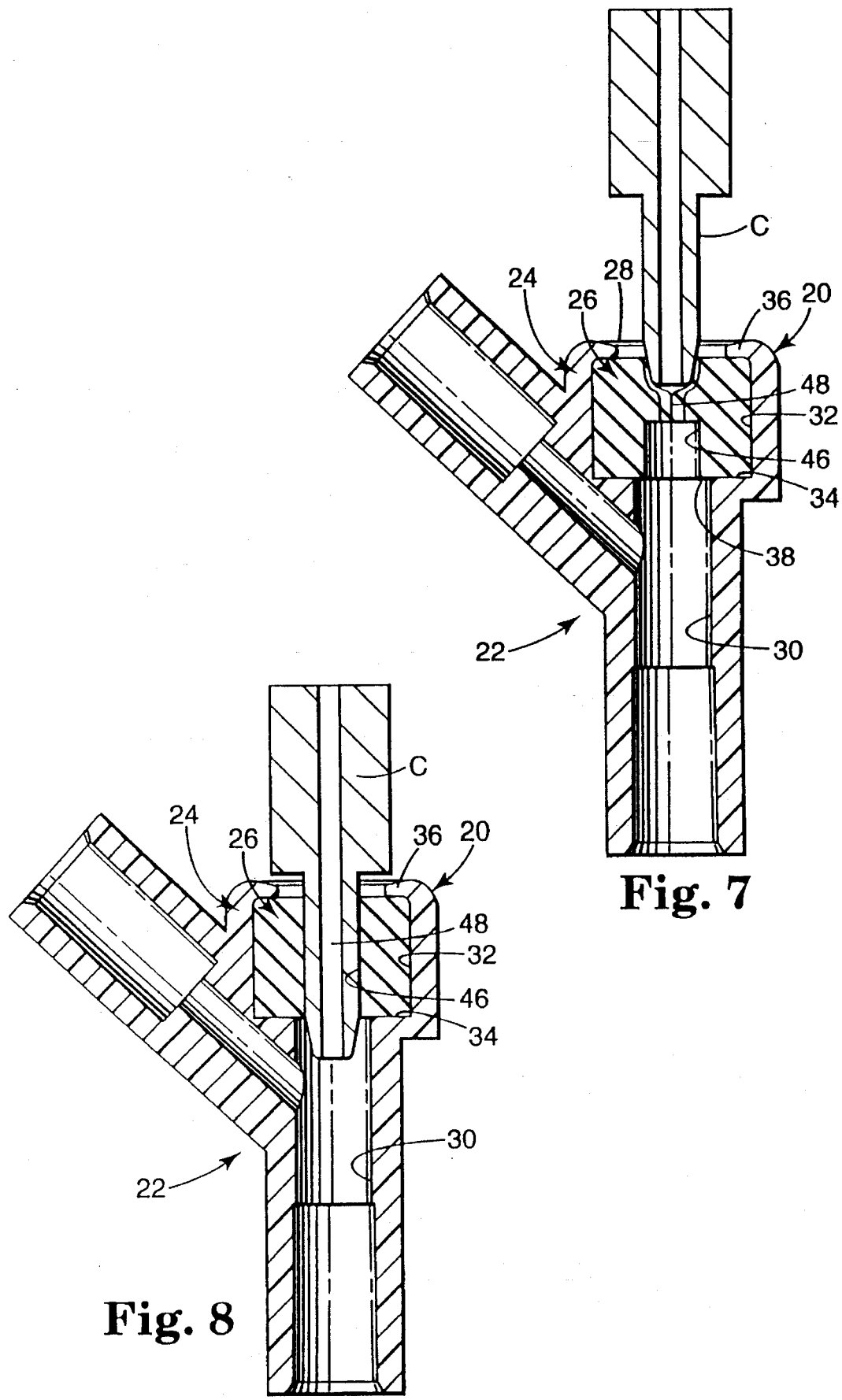
FIG. 7 is a longitudinal cross-sectional view of a Y-site IV injection site incorporating an injection site constructed according to the principles of this invention, showing a blunt cannula partially inserted into the injection site.
FIG. 8 is a longitudinal cross-sectional view of a Y-site IV injection site incorporating-an injection site constructed according to the principles of this invention, showing a blunt cannula fully inserted into the injection site.

As shown in FIGS. 7 and 8, although the openings 48 are significantly smaller in size, a blunt cannula C can still be introduced into one of the openings 48, and through the septum 26. For example, the cannulae available under the trade designation "Needle-Less Injection Cannula" from Baxter International, Inc., Deerfield, Ill., have an outer diameter of approximately 0.10 inches (2.5 mm), and the cannulae available under the trade designation "LifeShield Infection Control System" from Abbott Laboratories, Inc., Abbott Park, Ill., has an outer diameter of approximately 0.05 inches (1.27 mm).

Despite the size difference that will usually be encountered between the cannula and the openings 48, the septum 26 can typically accommodate the cannula without tearing. It is theorized that the plurality of openings 48 provided in the septum 26 relieve some of the stresses that would normally be associated with inserting a cannula into a single small opening 48 in the septum 26.

The septum material displaced by the cannula causes the bore 46 to gradually contract (compare FIG. 7 with FIG. 2), until the bore 46 closely surrounds and provides additional seal between the septum 26 and the cannula C (see FIG. 8).

Although not depicted, it will be understood that use of a sharp penetrator, such as a needle, will not typically displace as much of the septum material as will insertion of a blunt cannula because the needle diameter is smaller than the cannula diameter. In that situation, adequate sealing between the needle and the septum 26 is provided by the fit between the opening 48 and the needle.

Referring now to FIG. 9, an alternate embodiment of a septum 126 according to the present invention is depicted. In the septum 126, no bore is provided as described above. In this embodiment, adequate sealing will be provided between a cannula or needle and the opening 148 through which the cannula or needle is inserted solely by the compression of the septum material on the penetrator.

A further alternate variation in septums according to the present invention can include septums which are sized so as to fit within a housing without substantial compression. Sealing of the plurality of openings formed in such a septum would be provided by the elastomeric nature of the material from which the septum is formed.

A still further variation in septums according to the present invention is in the length of the openings 48 in a septum. Although it is preferred that the openings 48 be formed completely through the septum 26, it is contemplated that the openings could terminate just before perforating the inside and 38. Such a septum 26 may provide a more positive seal before perforation by a cannula or needle when first used for injection or sampling.

As various changes could be made in the above constructions and methods without departing from the scope of the invention, it is intended that all matter contained in the above description or shown in the accompanying drawing be interpreted as illustrative and not in a limiting sense.

We claim:

1. A site adapted to receive blunt or sharp penetrators, the site comprising:

a) a housing having an outside end and a passageway extending inwardly from the outside end, the passageway having an inside diameter and defining an axial direction;

b) an elastomeric septum located in the passageway of the housing, the septum having inside and outside ends relative to the housing; and c) a plurality of openings extending substantially through the septum from the inside end to the outside end generally in the axial direction, wherein the septum has an outside diameter larger than the inside diameter of the passageway such that the septum is radially compressed within the housing, wherein the plurality of holes are normally sealed when the septum is located in the passageway of the housing;

the housing supporting the septum such that a blunt cannula penetrate one of the openings in the septum rather than merely deflect the septum when the blunt cannula is pressed against the outside end of the septum, with the elastomeric material of the septum sealingly engaging the blunt cannula to prevent leakage and maintaining the other openings in the septum in sealed condition.

2. A site according to claim 1, wherein the plurality of openings are located in a pattern centered about an axial center of the septum.

3. A site according to claim 2, wherein the pattern is generally circular and has a diameter about half as long or less as a diameter of the septum at its outside end.

4. A site according to claim 2, wherein the septum further comprises a bore in the inside end, the bore being formed in the axial direction, and further wherein each of the plurality of openings lies within a diameter of the bore.

5. A site according to claim 2, wherein the plurality of openings comprises at least three holes.

6. A site adapted to receive blunt or sharpened penetrators, the site comprising:

a) a housing having an outside end and a passageway extending inwardly from the outside end, the passageway having an inside diameter and defining an axial direction;

b) an elastomeric septum located in the passageway of the housing, the septum having inside and outside ends relative to the housing, the septum further comprising a bore formed in the inside end of the septum, the bore being formed in the axial direction; and c) a plurality of openings extending substantially through the septum from the inside end to the outside end generally in the axial direction, the plurality of openings being located in a generally circular pattern centered about an axial center of the septum, the pattern having a diameter about half as long or less as a diameter of the septum at its outside end, wherein each of the plurality of openings lies within a diameter of the bore, and further, wherein the septum comprises an outside diameter larger than the inside diameter of the passageway such that the septum is radially compressed within the housing, wherein the plurality of openings are normally sealed when the septum is located in the passageway of the housing;

the housing supporting the septum such that a blunt cannula will penetrate one of the openings in the septum rather than merely deflect the septum when the blunt cannula is pressed against the outside end of the septum, with the elastomeric material of the septum sealingly engaging the blunt cannula to prevent leakage and maintaining the other openings in the septum in sealed condition.

7. A site according to claim 6, wherein the plurality of openings comprises at least three holes.

8. A method of using a site with a blunt cannula, the method comprising the steps of:

a) providing a blunt cannula having a cross section;

b) providing an injection or sampling site comprising a housing having an outside end and a passageway extending inwardly from the outside end, the passageway defining an axial direction, the site further comprising an elastomeric septum located in the passageway of the housing, the septum having inside and outside ends relative to the outside end of the housing and a multiplicity of openings extending substantially through the septum from the inside end to the outside end generally in the axial direction, each opening having a cross section substantially smaller than the cross section of the blunt cannula, the septum being supported within the housing such that a blunt cannula will penetrate one of the openings in the septum rather than merely deflect the septum when the blunt cannula is pressed against the outside end of the septum, with the elastomeric material of the septum sealingly engaging the blunt cannula to prevent leakage;

c) inserting the blunt cannula through one of the openings through the septum; and d) sealingly engaging the inserted blunt cannula with the septum.

9. A method according to claim 8, further comprising the step of compressing the septum transverse to the axial direction.

10. A method according to claim 8, further comprising inserting a sharp penetrator through at least one of the plurality of openings when a blunt penetrator is not inserted through any of the holes in the septum.

11. A method according to claim 8, wherein the plurality of openings are located in a pattern generally centered about an axial center of the septum; the step of inserting a blunt penetrator including inserting the blunt penetrator through one of the openings located in the pattern.

12. A method according to claim 11, wherein the pattern is generally circular and has a diameter about half as long or less as a diameter of the septum at its outside end; the step of inserting the blunt penetrator through one of the openings located in the pattern comprising inserting the blunt penetrator through one of the openings located in the generally circular pattern.

13. A method of assembling an injection or sampling site comprising the steps of:

molding a housing having an outside end and a passageway extending inwardly from the outside end, the passageway defining an axial direction and having an inside diameter;

molding an elastomeric septum having inside and outside ends relative to the outside end of the housing, and forming a multiplicity of openings extending substantially through the septum from the inside end to the outside end generally in the axial direction, the septum having an outside diameter greater than the inside diameter of the passageway of the housing;

inserting the septum into the housing to radially compress the septum within the housing; and forming structure in the housing to support the septum from deflection when a blunt cannula is pressed against the outside surface of the septum such that the blunt cannula will pass through one of the multiplicity of openings rather than merely deflect the septum.

14. A method according to claim 13, wherein the step of molding an elastomeric septum and forming a multiplicity of openings further comprises molding the septum with the plurality of openings formed therein.

15. A method according to claim 13, wherein the step of molding an elastomeric septum and forming a multiplicity of openings comprises forming the plurality of openings after the septum is formed.

16. A method according to claim 13, wherein the step of molding an elastomeric septum further comprises molding a bore in the inside end of the septum, the bore having a diameter, the bore being formed in the axial direction, and further wherein each of the plurality of openings has a longitudinal axis extending from the opening within the diameter of the bore.

17. A site adapted to receive blunt or sharp penetrators, the site comprising:
- a housing having an outside end and a passageway extending inwardly from the outside end, the passageway having an inside diameter and defining an axial direction;
- an elastomeric septum located in the passageway of the housing, the septum having inside and outside ends relative to the housing, and a multiplicity of openings extending substantially through the septum from the inside end to the outside end generally in the axial direction, the openings being normally sealed to prevent fluid leakage through the septum;
- the housing supporting the septum such that a blunt cannula will penetrate one of the openings in the septum rather than merely deflect the septum when the blunt cannula is pressed against the outside end of the septum, with the elastomeric material of the septum sealingly engaging the blunt cannula to prevent leakage.

18. A site according to claim 17 wherein the septum has an outside diameter, the housing including ledges defining a septum-receiving portion of the passageway, the ledges defining openings having a diameter substantially smaller than the diameter of the septum to support the septum against deflection when a blunt cannula is introduced into the septum.

19. A site according to claim 18 wherein, before assembly of the septum in the passageway of the housing, the septum has an outside diameter larger than the inside diameter of the septum-receiving portion of the passageway such that the septum is radially compressed within the housing.

20. A site according to claim 19, wherein the plurality of openings are located in a pattern centered about an axial center of the septum.

21. A site according to claim 20, wherein the pattern is generally circular and has a diameter about half as long or less as a diameter of the septum at its outside end.

22. A site according to claim 21, wherein the septum further comprises a bore extending into the septum from the inside end of the septum, the bore being formed in the axial direction, the bore having a diameter, each of the multiplicity of openings having a longitudinal axis extending from the opening within a diameter of the bore.

23. A site according to claim 22, wherein the multiplicity of openings comprises at least three holes.

24. A site according to claim 17, wherein the multiplicity of openings comprises at least ten holes.

25. A site according to claim 24, wherein the multiplicity of openings comprises at least fifteen holes.

* * * * *

UNITED STATES PATENT AND TRADEMARK OFFICE
CERTIFICATE OF CORRECTION

PATENT NO. : 5,520,641
DATED : May 28, 1996
INVENTOR(S) : Brett A. Behnke and Gary A. Thill It is certified that error appears in the above-indentified patent and that said Letters Patent is hereby corrected as shown below:

Col. 2, line 34, "and-bore" should read --and bore--.
Col. 2, line 44, "incorporating-an" should read --incorporating an--.
Col. 2, line 64, "housings" should read --housing--.
Col. 3, line 10, "under-the" should read --under the--.
Col. 3, line 49, "secured-in" should read --secured in--.
Col. 4, line 55, "Central" should read --central--.
Col. 7, line 20, after "cannula" insert --will--.

Signed and Sealed this

Twenty-fourth Day of September, 1996

Attest:

BRUCE LEHMAN

*Attesting Officer*     *Commissioner of Patents and Trademarks*